US006561012B1

United States Patent
Sadler

(10) Patent No.: US 6,561,012 B1
(45) Date of Patent: May 13, 2003

(54) CONTINUOUS FLOW MOISTURE ANALYZER

(75) Inventor: William G. Sadler, Scottsdale, AZ (US)

(73) Assignee: Arizona Instrument LLC, Tempe, AZ (US)

( * ) Notice: Subject to any disclaimer, the term of this patent is extended or adjusted under 35 U.S.C. 154(b) by 0 days.

(21) Appl. No.: 09/693,645

(22) Filed: Oct. 20, 2000

(51) Int. Cl.[7] .......................... G01N 25/56; G01N 5/02
(52) U.S. Cl. ................. 73/73; 73/76; 73/29.01
(58) Field of Search .................... 73/76, 73, 19.01, 73/29.01, 29.03, 29.04

(56) References Cited

U.S. PATENT DOCUMENTS

| 4,838,705 A | * | 6/1989 | Byers, Jr. et al. | ............. 374/14 |
| 5,431,067 A | * | 7/1995 | Anderson | ................ 73/863.86 |
| 5,712,421 A | * | 1/1998 | Raisanen | ................... 73/19.01 |

* cited by examiner

Primary Examiner—Daniel S. Larkin
Assistant Examiner—Rodney Frank
(74) Attorney, Agent, or Firm—Jordan M. Meschkow; Richard E. Oney

(57) ABSTRACT

A continuous flow moisture analyzer (20) includes a coaxial needle (34) having first and second needle portions (36, 38). The first needle portion (36) receives a carrier gas (24) and expels the carrier gas (24) through an output orifice (60). The second needle portion (38) has an input orifice (62) for receiving the carrier gas (24) expelled from the output orifice (60). A housing (40) encloses the output orifice (60) and the input orifice (62) when the moisture analyzer (20) is in a standby mode to obtain a baseline moisture content of the carrier gas (24) within the moisture analyzer (20). A bottle (48) retains a sample material (50). When the analyzer (20) is in an active mode, the coaxial needle (34) penetrates a septum (52) of the bottle (48) to position the output and input orifices (60, 62) in the bottle (48). The carrier gas (24), expelled from the output orifice (60), absorbs moisture from the sample material (50) in the bottle (48). The expelled carrier gas (24) carrying the moisture is received at the input orifice (62) and is transported through the second needle portion (38) to a moisture sensor (70) which detects the moisture in the carrier gas (24).

30 Claims, 7 Drawing Sheets

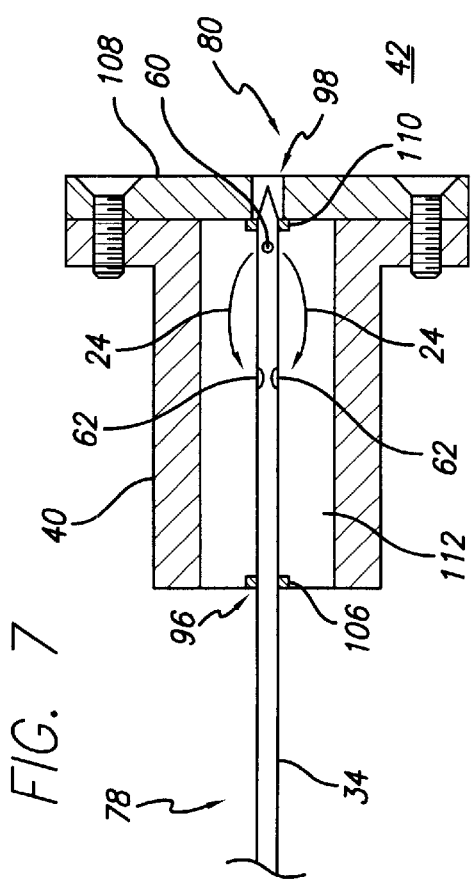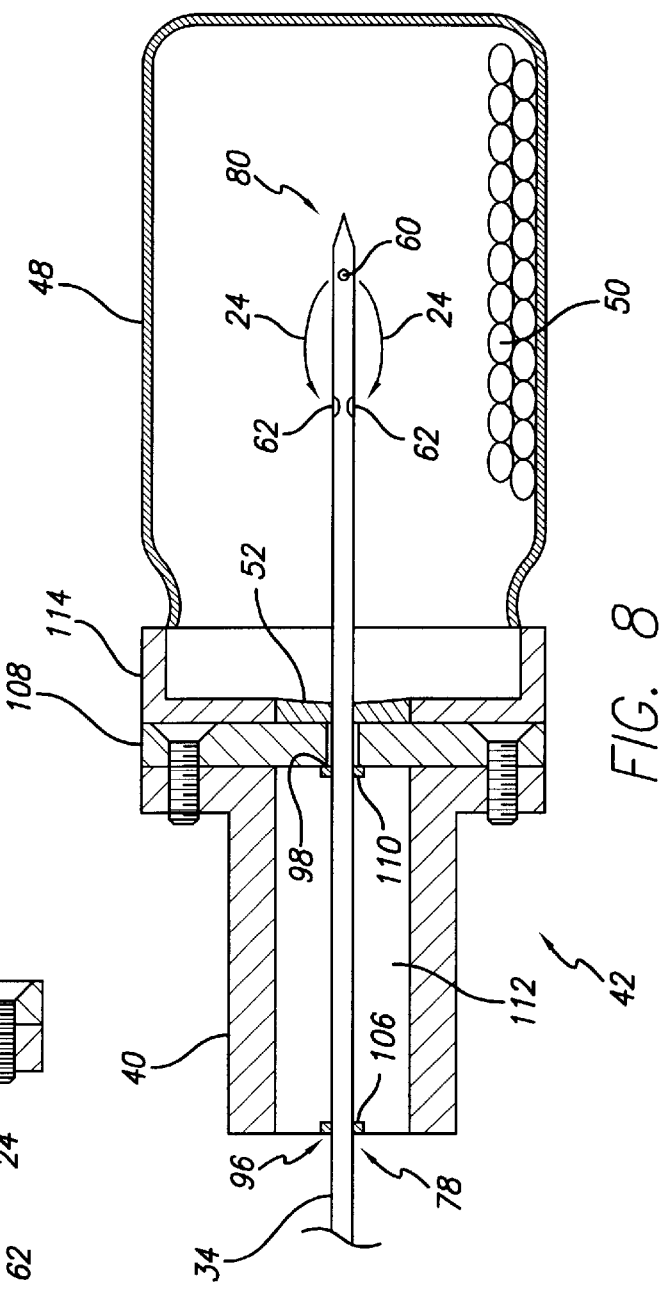

CONTINUOUS FLOW MOISTURE ANALYZER

TECHNICAL FIELD OF THE INVENTION

The present invention relates generally to moisture analyzers. More specifically, the present invention relates to a continuous flow moisture analyzer for determining the moisture content in a sample material under test.

BACKGROUND OF THE INVENTION

Various manufacturing processes, chemical reactions, and laws attendant certain industries require that the percentage of certain volatile fluids of interest present within a product be known. Indeed, the determination of moisture (or volatile) content in materials is of such importance in so many fields that a wide variety of devices and analytical methods have been developed to provide such information. One such analytical moisture analysis method is a chemical analysis method known as the Karl Fischer technique. The Karl Fischer moisture analysis technique is a method of titrating a test sample with a reagent to determine trace amounts of water in the test sample. Unfortunately, chemical analysis methods rely on the use of various reagents which may be toxic. Moreover, such chemical analysis methods usually require very skilled operators and are often quite time consuming.

Moisture analysis devices include, for example, vacuum ovens and convection ovens which heat a test sample of the product to a temperature commensurate with the volatile fluid of interest to cause evaporation of such fluid. Devices of this type are often referred to as loss on drying analyzers. Using a loss on drying moisture analyzer, the resulting reduction in weight of the test sample provides data for computing the percent by weight of the volatile fluid of interest in the test sample. Various computational techniques may be employed to forecast the percentage determination based upon the initial weight loss rate. Such computational approximations reduce the time required to complete a test without serious derogation of the accuracy of the determination. Loss on drying techniques are limited to approximately 0.1% minimum moisture loss due to secondary effects such as convective air currents, buoyancy effects, and temperature gradients. In addition, loss on drying techniques can sustain some degree of measurement error relative to the accuracy of the scale used for weighing the test sample.

Other moisture analysis devices employ sensors that measure the quantity of volatile fluid in a gas stream to determine the amount of volatile fluid in a test sample. For example, one such moisture analyzer includes a test sample heater, a dry carrier gas flow system, and a moisture transducer. The moisture analyzer heats a sample of test material contained in a septum bottle. The dry gas is injected into the septum bottle and absorbs the moisture out of the sample material. The dry gas, carrying the moisture from the sample, is ejected from the septum bottle and transported to the moisture transducer where the moisture content of the flowing gas is measured. A processor then integrates the varying moisture signal and converts the integrated signal to total moisture content. Using the sample weight and the total moisture content value, the moisture concentration in the test sample is subsequently calculated.

Unfortunately, problems such as pre-existing moisture levels, transient response times, and contamination render the measurement of moisture content inaccurate. In one such moisture analyzer, uncontrolled moisture can be introduced into the dry carrier gas flow system. This uncontrolled moisture results in a non-consistent baseline, which consequently leads to inaccuracy in the measurement of the moisture content in the sample material.

SUMMARY OF THE INVENTION

Accordingly, it is an advantage of the present invention that a continuous flow moisture analyzer is provided.

It is another advantage of the present invention the continuous flow moisture analyzer efficiently and accurately determines the moisture content in a sample of dry material.

It is another advantage of the present invention that the continuous flow moisture analyzer accurately determines the moisture content in a sample material by substantially preventing the introduction of uncontrolled moisture in the gas flow system of the moisture analyzer.

The above and other advantages of the present invention are carried out in one form by a continuous flow moisture analyzer including a first needle portion having a first channel for receiving a carrier gas and having an output orifice from the first channel for expelling the carrier gas and a second needle portion having an input orifice for receiving the carrier gas expelled from the output orifice and having a second channel in communication with the input orifice for transporting the carrier gas. A housing encloses the output orifice and the input orifice when the moisture analyzer is in a standby mode. A bottle retains a sample material when the moisture analyzer is in an active mode. The bottle has a septum configured to face the housing, the first and second needle portions penetrating the septum to position the output and input orifices in the bottle. The carrier gas expelled from the output orifice absorbs moisture from the sample material, and a moisture sensor in fluid communication with the second channel detects moisture in the carrier gas.

The above and other advantages of the present invention are carried out in another form by a continuous flow moisture analyzer. The continuous flow moisture analyzer includes a coaxial needle having a first end and a second end. The coaxial needle includes a first needle portion having a first channel for receiving a carrier gas and having an output orifice from the first channel for expelling the carrier gas. The coaxial needle further includes a second needle portion having an input orifice for receiving the carrier gas expelled from the output orifice and having a second channel in communication with the input orifice for transporting the carrier gas. The output orifice and the input orifice are located proximate the second end. A housing encloses the output orifice and the input orifice when the moisture analyzer is in a standby mode. The housing includes a track in nonmoving relation with the coaxial needle, and a sleeve slidably coupled to the track. A bottle retains a sample material and is configured to abut the sleeve when the moisture analyzer is in an active mode. The bottle has a septum facing the sleeve. When the bottle abuts the sleeve, the sleeve retracts along the track to allow the coaxial needle to penetrate the septum to position the output and input orifices in the bottle. The carrier gas expelled from the output orifice absorbs moisture from the sample material, and a moisture sensor in fluid communication with the second channel detects the moisture in the carrier gas.

The above and other advantages of the present invention are carried out in yet another form by a continuous flow moisture analyzer. A continuous flow moisture analyzer a first needle portion having a first channel for receiving a carrier gas and having an output orifice from the first channel for expelling the carrier gas and a second needle portion having an input orifice for receiving the carrier gas expelled from the output orifice and having a second channel in communication with the input orifice for transporting the carrier gas. A housing encloses the output orifice and the input orifice when the moisture analyzer is in a standby mode. The housing includes a track in non-moving relation with the coaxial needle, and a sleeve sidably coupled to the track. A bottle retains a sample material when the moisture analyzer is in an active mode. The bottle has a septum configured to face the housing. The moisture analyzer further includes a transport mechanism for conveying the bottle toward the housing so that the first and second needle portions penetrate a center portion of the septum to position the output and input orifices in the bottle. The carrier gas expelled from the output orifice absorbs moisture from the sample material, and a moisture sensor in fluid communication with the second channel detects the moisture in the carrier gas.

BRIEF DESCRIPTION OF THE DRAWINGS

A more complete understanding of the present invention may be derived by referring to the detailed description and claims when considered in connection with the Figures, wherein like reference numbers refer to similar items throughout the Figures, and:

FIG. 7 shows a sectional side view of the housing of FIG. 5 enclosing the coaxial needle in a standby mode;

FIG. 8 shows a sectional side view of the housing of FIG. 6 with the coaxial needle located in a bottle retaining a sample material in an active mode;

DETAILED DESCRIPTION OF THE PREFERRED EMBODIMENTS

Figure 1:
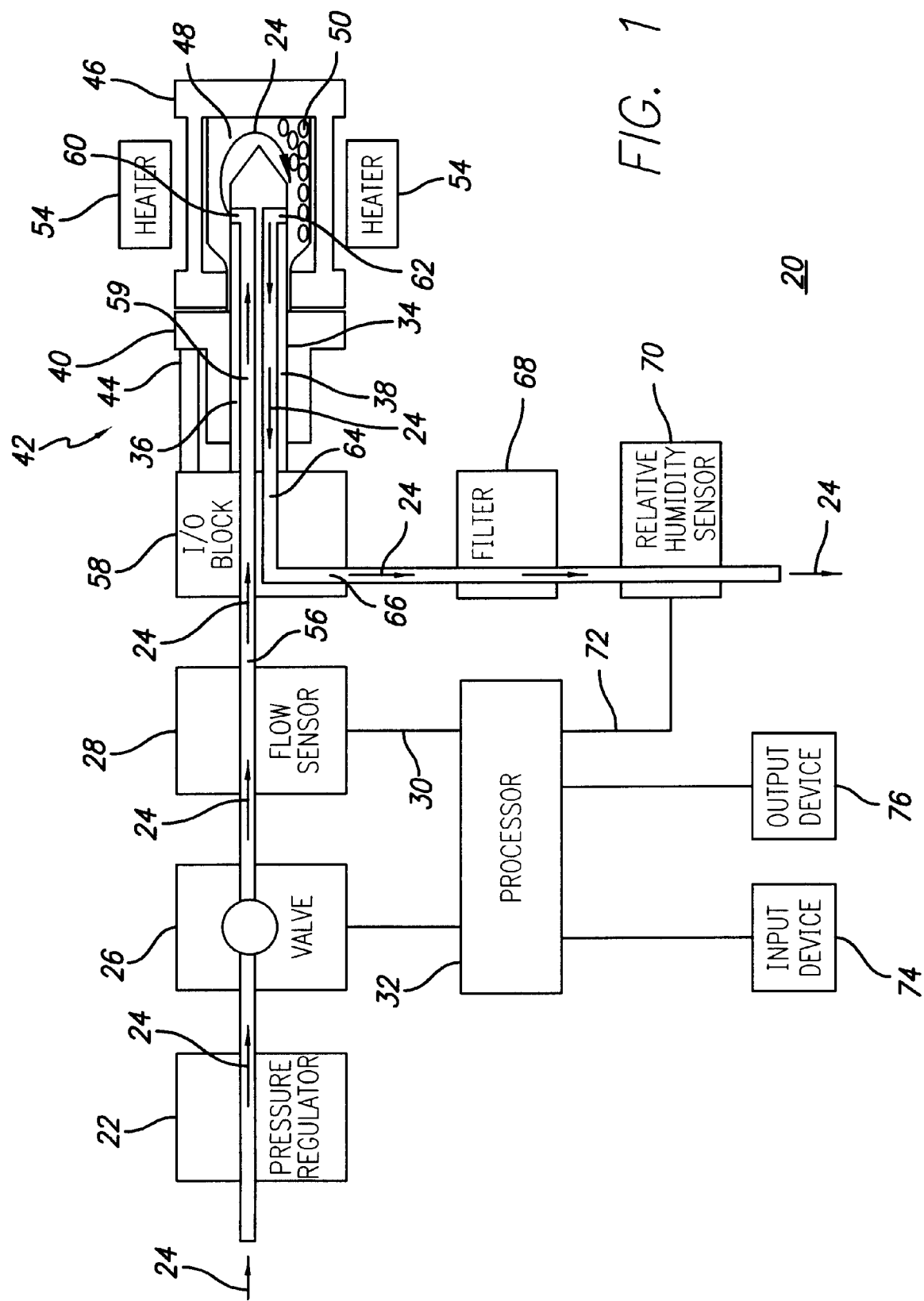
FIG. 1 shows a block diagram of a continuous flow moisture analyzer in accordance with a preferred embodiment of the present invention.

FIG. 1 shows a block diagram of a continuous flow moisture analyzer 20 in accordance with a preferred embodiment of the present invention. Moisture analyzer 20 is used primarily for determining the moisture content, i.e., the volatile liquid such as water, in a solid sample material under test. Exemplary solid sample materials include plastic pellets, food products, such as cereal, freeze dried pharmaceuticals, and so forth. Moisture analyzer 20 is configured to evaporate the moisture present within a sample material. This moisture is absorbed by a carrier gas passing over the sample material. The carrier gas is transported to a moisture sensor, which subsequently detects the moisture in the carrier gas.

Moisture analyzer 20 includes a pressure regulator 22 configured to receive a flow of carrier gas, represented by arrows 24. Carrier gas 24 may be dry nitrogen, dry air, or any other gas that can effectively absorb and carry moisture. Pressure regulator 22 provides carrier gas 24 to a valve 26 at a predetermined pressure. In a preferred embodiment, the predetermined pressure is approximately one and a half pounds per square inch.

Valve 26 is a restrictor valve that receives carrier gas 24 output by pressure regulator 22 and provides carrier gas 24 at a controlled flow rate. In particular, valve 26 has an orifice of approximately 0.15 mm (0.006 inches) for controlling the flow rate of carrier gas 24 to approximately one hundred milliliters per minute.

An output of valve 26 is in communication with a flow sensor 28. Flow sensor 28 measures a mass flow of carrier gas 24 as carrier gas 24 passes flow sensor 28. The mass flow is the mass of a fluid substance (e.g., carrier gas 24) that passes a specified unit area in a unit amount of time. Flow sensor 28 has an output in communication with a processor 32 for providing a mass flow signal 30, responsive to the flow rate of carrier gas 24, through an analog-to-digital converter (not shown) to a processor 32.

Moisture analyzer 20 further includes a coaxial needle 34 having a first needle portion 36 and a second needle portion 38. Coaxial needle 34 passes through a sleeve 40 of a housing 42, sleeve 40 being slidably coupled to a track 44 of housing 42. A transport mechanism 46 conveys a bottle 48 toward housing 42. Bottle 48 is configured to retain a sample material 50. Bottle 48 includes a septum 52 (see FIG. 8) configured to face housing 42 such that coaxial needle 34 penetrates through septum 52 into bottle 48.

A heater 54 surrounds bottle 48 and is configured to heat sample material 50 to a predetermined temperature at a predetermined rate to evaporate the volatile liquid from sample material 50. The predetermined temperature and rate, controlled by processor 32, depend upon the characteristics of both the sample and the volatile liquid of interest. A resistive temperature device (not shown) may be used to read the temperature of heater 54.

Carrier gas 24 flows from valve 26 via flow sensor 28 to an inlet 56 of first needle portion 36 of coaxial needle 34. As such, pressure regulator 22 and valve 26 are in fluid communication with first needle portion 36. Inlet 56 is generally located in an inlet/outlet (I/O) block 58 of moisture analyzer 20. Carrier gas 24, received at inlet 56 is conveyed through a first channel 59 of first needle portion 36 to an output orifice 60.

Carrier gas 24 is expelled from first channel 59 via output orifice 60 of first needle portion 36 into bottle 48. Carrier gas 24 absorbs evaporated moisture from sample material 50 as sample material 50 is heated. Carrier gas 24, expelled from output orifice 60 of first needle portion 36, is received at an input orifice 62 of second needle portion 38 of coaxial needle 34. Second needle portion 38 includes a second channel 64 in communication with input orifice 62 for transporting carrier gas 24.

Carrier gas 24 is expelled from an outlet 66 of second needle portion 38 located in inlet/outlet block 58. Carrier gas 24 flows from second channel 64 through outlet 66 to a filter 68. During the heating of sample material 50 within bottle 48, particulate matter of sample material 50 may be inadvertently conveyed by carrier gas 24. Such particulate matter may jeopardize the integrity and accuracy of analysis of the moisture in carrier gas 24 and/or undesirably cause particulate matter to be exhausted from moisture analyzer 20 with carrier gas 24. To eliminate such particulate matter, filter 68 may be employed to filter carrier gas 24 flowing from outlet 66.

Following filtering at filter 68, carrier gas 24 flows to a relative humidity sensor 70. Relative humidity sensor 70 is a moisture sensor for detecting moisture in carrier gas 24. Relative humidity sensor 70 has an output in communication with a processor 32 for providing a percent relative humidity signal 72, responsive to the relative humidity of carrier gas 24, through an analog-to-digital converter (not shown) to processor 32. In a preferred embodiment, moisture analyzer 20 employs a relative humidity sensor. However, is should be apparent that other moisture sensors may be used. In addition, a moisture detecting reagent maybe used as a moisture sensor in an alternative embodiment of the present invention.

Processor 32 subsequently computes a moisture content of carrier gas 24 as a volume per unit of time in response to mass flow signal 30 received from flow sensor 28 and percent relative humidity signal 72 received from moisture sensor 70. Following detection of the moisture content in carrier gas 24, carrier gas 24 is exhausted from continuous flow moisture analyzer 20.

Controls for the various sequential steps, pressure, flow rates, predetermined temperature and rate, and so forth are performed by processor 32. Processor 32 is in communication with an input device 74 and an output device 76. Input device 74 can encompass a keypad, keyboard, mouse, pointing device, or other devices providing input to processor 32. Such input may include, for example, material sample identification, lot or product ID number, test parameters, test duration, and so forth. Output device 76 can encompass a display, a printer, or other devices providing output from processor 32. Such output may include, material sample identification, test results in parts-per-million, test results in percent moisture, test results in total micrograms of water, and so forth.

The moisture content of carrier gas 24 is computed relative to a baseline moisture content of carrier gas 24. In other words, processor 32 initially computes a moisture content of carrier gas 24 in a standby mode, i.e., prior to coaxial needle 34 penetrating septum 52 (FIG. 8) of bottle 48. The moisture content of carrier gas 24 is then computed in an active mode, i.e., after coaxial needle 34 has penetrated septum 52 of bottle 48. Processor 32 subsequently computes a difference from the baseline moisture content responsive to the moisture detected during the active mode to obtain a moisture content of sample material 50.

The structure of continuous flow moisture analyzer 20 substantially prevents the entry of uncontrolled moisture into the carrier gas flow portions of analyzer 20. In particular, uncontrolled moisture is prevented from entering analyzer 20 and being detected by relative humidity sensor 70 through the construction of coaxial needle 34 and housing 42, as will become readily apparent in the ensuing discussion.

Figure 2:
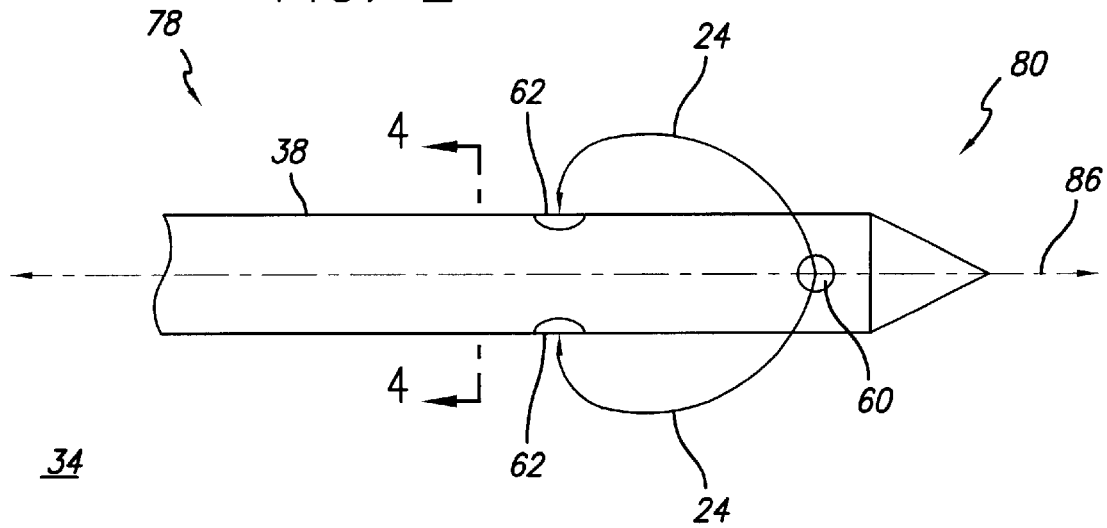
FIG. 2 shows a side view of a coaxial needle of the moisture analyzer.
Figure 3:
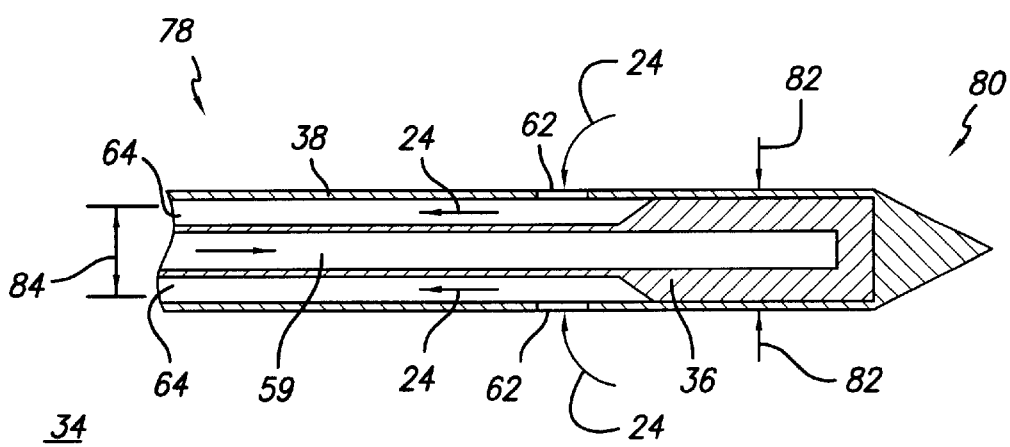
FIG. 3 shows a sectional side view of the coaxial needle of FIG. 2.
Figure 4:
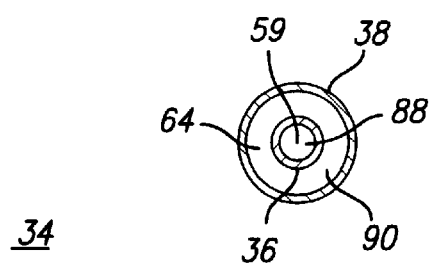
FIG. 4 shows a cross-sectional view of the coaxial needle along line 4—4 in FIG. 2.

Referring to FIGS. 2–4, FIG. 2 shows a side view of coaxial needle 34 of moisture analyzer 20 (FIG. 1). FIG. 3 shows a sectional side view of coaxial needle 34, and FIG. 4 shows a cross-sectional view of coaxial needle 34 along line 4—4 in FIG. 2.

Coaxial needle 34 is a two part needle assembly formed from first needle portion 36 and second needle portion 38. First needle portion 36 is a plunger structure through which first channel 59 is directed from a first end 78 to a second end 80 of coaxial needle 34. First needle portion 36 exhibits an outer diameter 82 at its widest point proximate second end 80.

Second needle portion 38 is generally tube shaped having a sharp point at second end 80 of coaxial needle 34. Second channel 64 is directed from first end 78 to second end 80 of coaxial needle. Second channel 64 exhibits an inner diameter 84. Inner diameter 84 is greater than outer diameter 82 of second needle portion 36, so that first needle portion 36 is positioned within second channel 64 to form coaxial needle 34. Thus, first and second needle portions 36 and 38, respectively, of coaxial needle 34 have a common longitudinal axis 86.

Coaxial needle 34 is shown having one output orifice 60 and two input orifices 62. However, it should be understood that coaxial needle 34 may include any number of output and input orifices to best accommodate the flow of carrier gas 24 from output orifice 60 to input orifice 62. Output orifice 60 of first needle portion 36 and input orifice 62 of second needle portion 38 are located proximate second end 80 with output orifice 60 being nearer to second end 80.

Input orifices 62 are longitudinally offset along second needle portion 38 from the location of output orifice 60. That is, input orifices 62 are located farther away from second end 80 than output orifice 60. Input orifices 62 are also circumferentially offset about second needle portion 38 from the location of output orifice 60. That is, input orifices 62 are rotated about the circumference of second needle portion 38 approximately ninety degrees out of alignment with output orifice 60. This longitudinal and circumferential offset of input orifice 62 relative to output orifice 60 causes carrier gas 24 to effectively circulate in bottle 48 (FIG. 1) to absorb moisture from sample material 50 prior to carrier gas 24 being received at input orifice 62.

First channel 59 exhibits a first cross-sectional gas flow area 88. Likewise, second channel 64 exhibits a second cross-sectional gas flow area 90. Second gas flow area 90 is substantially equivalent to first cross-sectional gas flow area. This equivalent size results in maximizing the flow of carrier gas 24 with minimum pressure drop.

FIGS. 2–4 show coaxial needle 34 in a preferred embodiment of the present invention. However, it should be understood that alternate structures of coaxial needle 34 may be envisioned. For example, the shape and placement of second needle portion 38 may be exchanged with the shape and placement of first needle portion 36. In such a configuration, second needle portion 38 may be located within a channel of first needle portion 36. Alternatively, first and second needle portions 36 and 38, respectively, may be two separate needles. As such, each of first and second needle portions 36 and 38 would include sharp points for penetrating septum 52 (FIG. 8).

Figure 5:
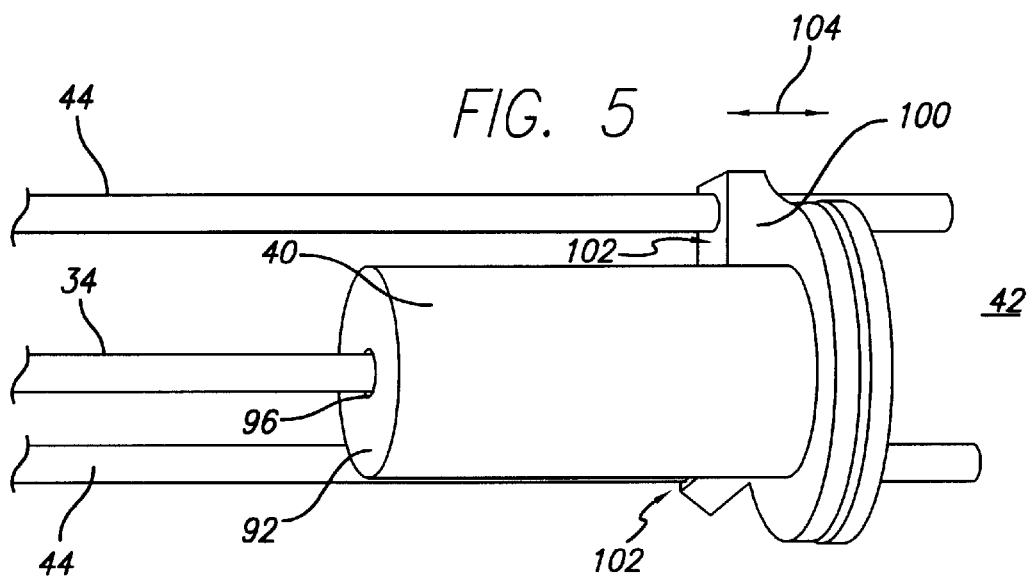
FIG. 5 shows a perspective view of a first side of a housing for enclosing the coaxial needle of the moisture analyzer.
Figure 6:
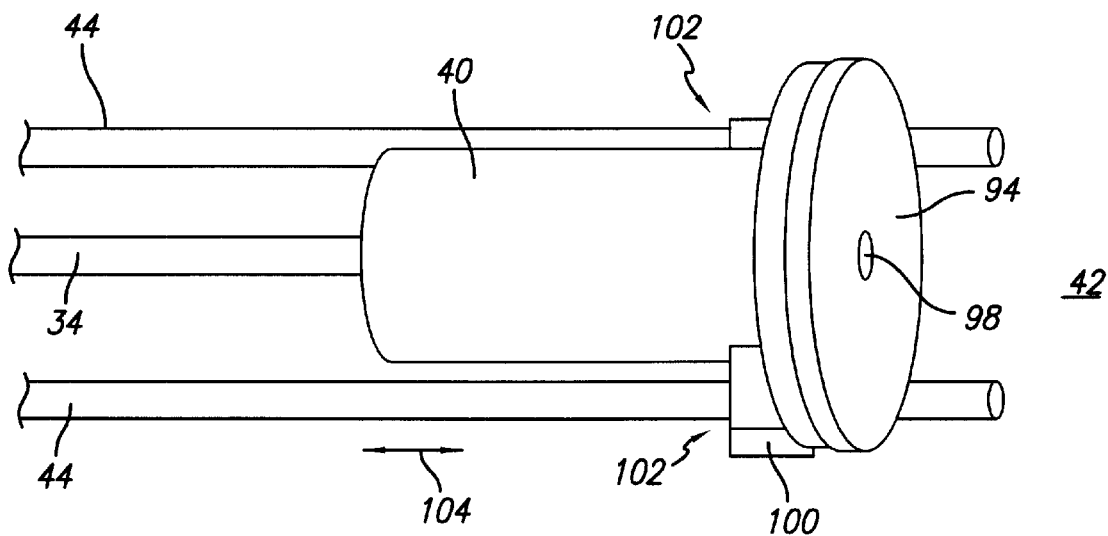
FIG. 6 shows a perspective view of a second side of the housing of FIG. 5.

Referring to FIGS. 5 and 6, FIG. 5 shows a perspective view of a first side 92 of sleeve 40 of housing 42 for enclosing coaxial needle 34 of moisture analyzer 20 (FIG. 1). FIG. 6 shows a perspective view of a second side 94 of sleeve 40 of housing 42. First side 92 includes a first opening 96 through which coaxial needle 34 extends. Second side 94 includes a second opening 98 through which coaxial needle 34 protrudes when moisture analyzer 20 (FIG. 1) is in the active test mode.

As discussed previously, housing 42 includes sleeve 40 slidably coupled to track 44. In a preferred embodiment, housing 42 includes two tracks 44. Tracks 44 may be coupled to inlet/outlet block 58 (FIG. 1) so that tracks 44 do not move relative to coaxial needle 34. A mounting fixture 100 is coupled to sleeve 40. Mounting fixture 100 includes passages 102 through which each of tracks 44 are directed. Sleeve 40 is then able to slide along tracks 44, the motion of which is represented by a bi-directional arrow 104.

FIG. 7 shows a sectional side view of sleeve 40 of housing 42 enclosing coaxial needle 34 in a standby mode. A first O-ring 106 is located in first opening 96. Second opening 98 is located in a cover portion 108 of sleeve 40 and a second O-ring 110 is located in second opening 98. Coaxial needle 34, surrounded by first O-ring 106 blocks first opening 96, and the second end 80 of coaxial needle 36, surrounded by second O-ring 110 blocks second opening 110. This blockage results in a sealed chamber 112 being formed within sleeve 40.

Thus, as shown in FIG. 7, when moisture analyzer 20 (FIG. 1) is in the standby mode, output orifice 60 and input orifice 62 are located within sealed chamber 112. As such, carrier gas 24 expelled at output orifice 60 is received at input orifice 62 without having absorbed uncontrolled moisture. Accordingly, the baseline moisture content of moisture analyzer 20 (FIG. 1) may be ascertained in the standby mode.

FIG. 8 shows a sectional side view of housing 42 with coaxial needle 34 located in bottle 48 in an active mode. In the active mode, second end 80 of coaxial needle 34 protrudes through second opening 98 and penetrates septum 52 in a lid 114 of bottle 48. This penetration is accomplished when lid 114 abuts cover portion 108 of sleeve 40. In response to the contact, sleeve 40 retracts by sliding along tracks 44 (FIGS. 5–6) so that coaxial needle 34 leaves sealed chamber 112 and penetrates septum 52. Thus, when moisture analyzer,20 (FIG. 1) is in the active mode, output orifice 60 and input orifice 62 are positioned within bottle 48. As such, carrier gas 24, expelled at output orifice 60, is received at input orifice 62 having absorbed moisture evaporated from sample material 50 as sample material 50 is heated.

The abutment of lid 114 with cover portion 108. results in minimal or negligible exposure of output orifice 60 and input orifices 62 to uncontrolled moisture from outside of moisture analyzer 20. Thus, the baseline moisture content determined in standby mode is a valid baseline from which a difference of moisture content may be computed in order to obtain a moisture figure for sample material 50.

Figure 9:
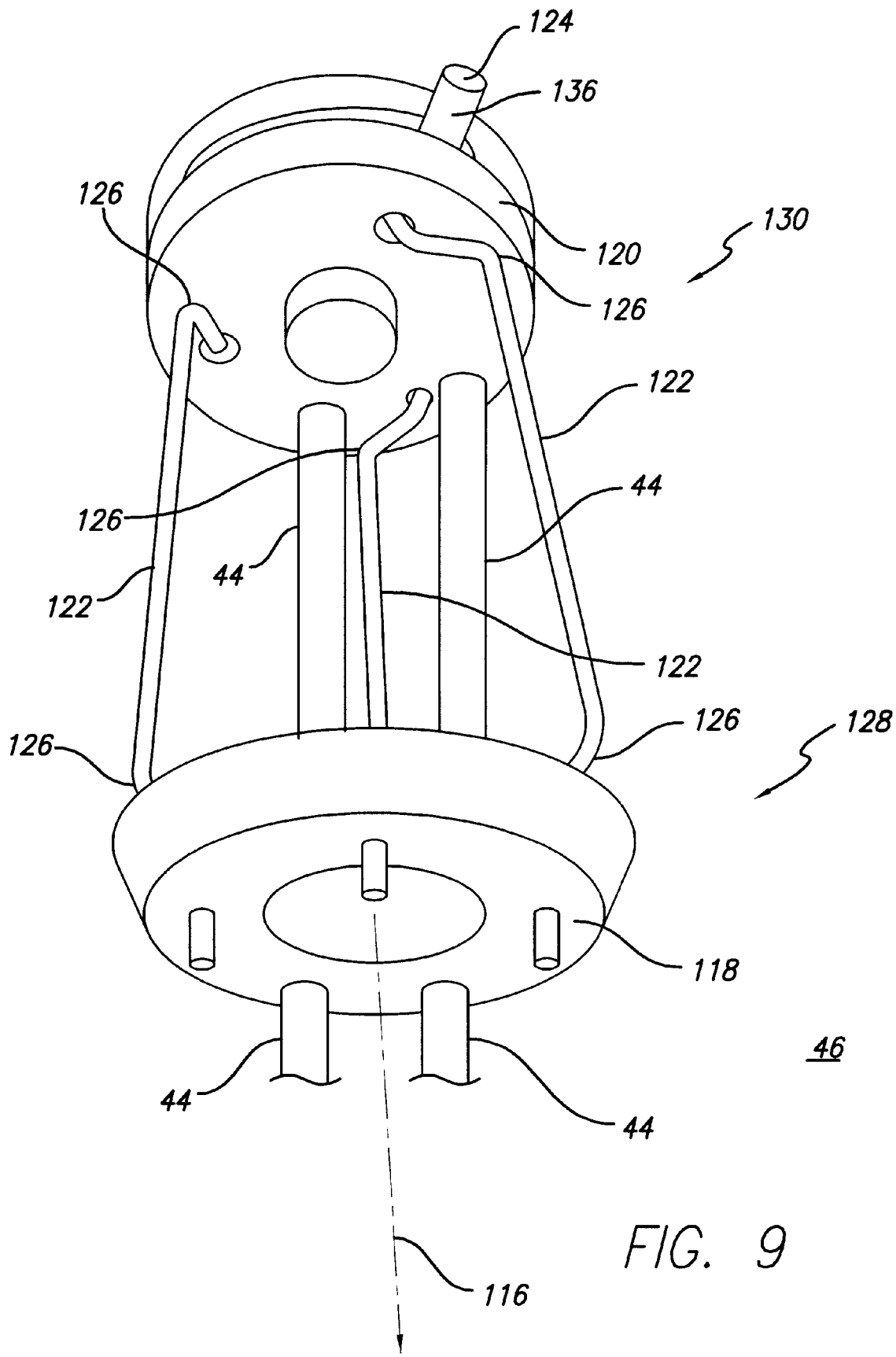
FIG. 9 shows a perspective view of a transport mechanism of the moisture analyzer for conveying the bottle.

FIG. 9 shows a perspective view of transport mechanism 46 of moisture analyzer 20 (FIG. 1) for conveying bottle 48 (FIG. 8) into abutment with sleeve 40 (FIG. 8) of housing 42. Like sleeve 40 (FIGS. 5–6) of housing 42, transport mechanism 46 may be slidably fixed to tracks 44 to align a center axis 116 of transport mechanism 46 with longitudinal axis 86 (FIG. 2) of coaxial needle 34 (FIG. 2). In addition, transport mechanism 46 may be transported along tracks 44 to an internal cavity (not shown) of moisture analyzer 20 (FIG. 1) in which the moisture analysis will occur. Transport mechanism 46 includes a top 118, a base 120, and retaining rods 122 disposed therebetween. Top 118 is configured to face housing 42 (FIG. 1), and base 120 includes an adjustment element 124. Retaining rods 122 are movably coupled to adjustment element 124 and top 118.

Each of retaining rods 122 has an elbow 126 at each of a first end 128 and a second end 130. When adjustment element 124 is actuated, retaining rods 122 concurrently pivot relative to top 118 and base 120 to bring elbows 126 toward center axis 116 of transport mechanism 46. Likewise, when adjustment element 124 is further actuated, retaining rods 122 concurrently pivot relative to top 118 and base 120 to bring elbows 126 away from center axis 116 of transport mechanism 46. In such a manner, transport mechanism 46 can convey bottles of varying diameters.

Figure 10:
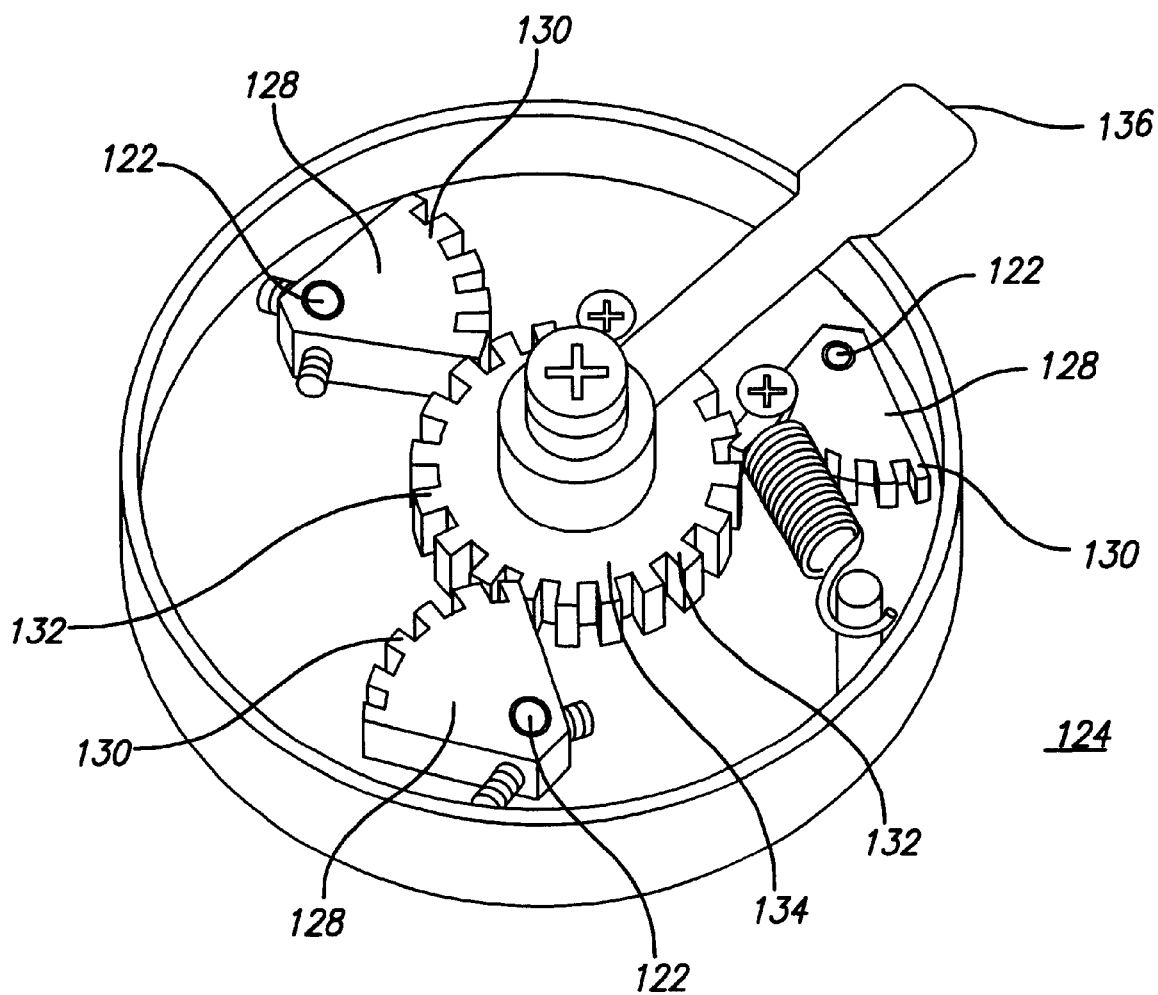
FIG. 10 shows a perspective view of an adjustment element of the transport mechanism of FIG. 9.

FIG. 10 shows a perspective view of adjustment element 124 of transport mechanism 46 (FIG. 9). Adjustment element 124 includes gears 128, each of which are coupled to one of retaining rods 122. Gears 128 include teeth 130 that mesh with corresponding teeth 132 of an actuating gear 134. When actuating gear 134 is put into action by movement of a lever 136, gears 128 concurrently move in order to affect the pivoting action of retaining rods 122.

Although adjustment element 124 is described using a gear based system. It should be understood that other mechanisms may be used to cause the concurrent pivoting action of retaining rods 122.

Figure 11:
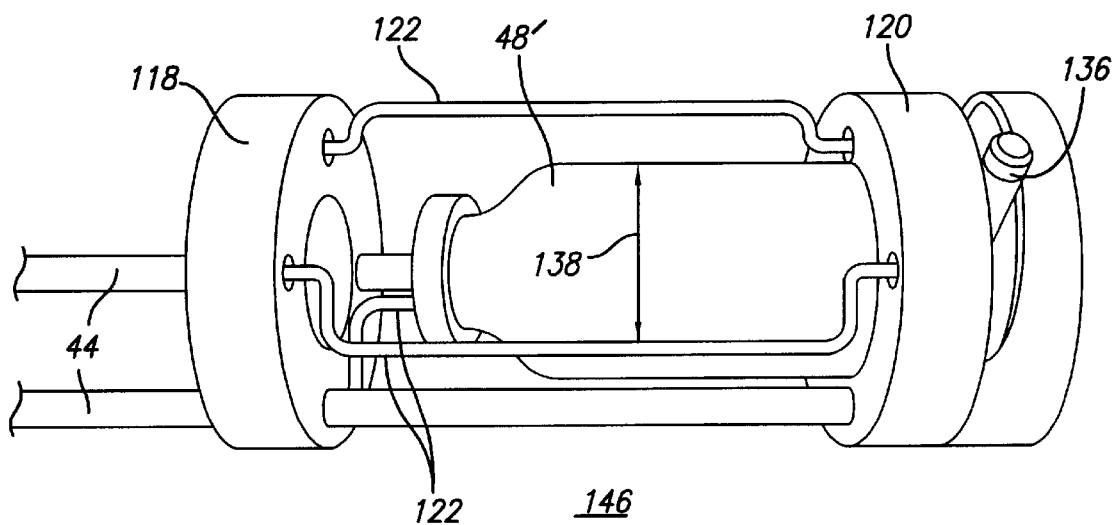
FIG. 11 shows a side view of the transport mechanism of FIG. 9 adjusted to convey a first bottle having a first diameter.
Figure 12:
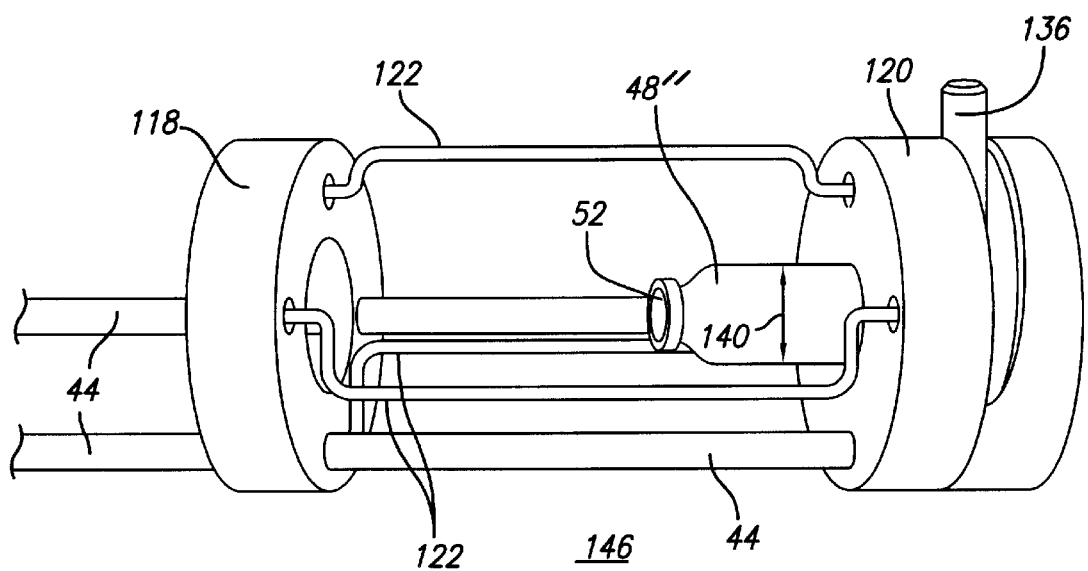
FIG. 12 shows a side view of the transport mechanism of FIG. 9 adjusted to convey a second bottle having a second diameter.

Referring to FIGS. 11–12, FIG. 11 shows a side view of transport mechanism 46 adjusted to convey a first bottle 48' having a first diameter 138. FIG. 12 shows a side view of transport mechanism 46 adjusted to convey a second bottle 48" having a second diameter 140. First diameter 138 of first bottle 48' differs from second diameter 140 of second bottle 48", in that first diameter 138 is larger than second diameter 140. The concurrent pivoting action of retaining rods 122 allows transport mechanism to readily adapt to bottles of varying sizes. Moreover, the concurrent pivoting action or retaining rods 122 results in bottles 48' and 48" maintaining alignment with coaxial needle 34 (FIG. 8) so that coaxial needle 34 penetrates septum 52.

In standby mode operation, moisture analyzer 20 (FIG. 1) is activated with coaxial needle 34 located in sealed chamber 112 (FIG. 7) of sleeve 40 (FIG. 7). When moisture analyzer 20 is activated, carrier gas 24 flows into sealed chamber 112 via first channel 59 (FIG. 3) of first needle portion 36 (FIG. 3). Carrier gas 24 is expelled from output orifice 60 (FIG. 7) into sealed chamber 112, and received at input orifice 62 of second needle portion 38. Carrier gas 24 is subsequently transported via second channel 64 (FIG. 3) to relative humidity sensor 70 to determine a baseline moisture content of continuous flow moisture analyzer 20. Moisture analyzer 20 may remain activated continuously in which case carrier gas 24 will flow through the system continuously. Alternatively, moisture analyzer 20 may be activated some predetermined period of time prior to performing moisture analysis of sample material 50 (FIG. 1).

Active mode operation is initiated following standby mode operation so that carrier gas 24 continuously flows during the entirety of standby mode and active mode operations. In active mode, bottle 48, or either of first and second bottles 48' and 48", is placed in transport mechanism 46 (FIG. 9). Lever 136 of adjustment element 124 (FIG. 9) is actuated to cause retaining rods 122 to pivot to retain bottle 48. Bottle 48 is positioned in retaining rods 122 so that lid 114 is positioned in a center opening of top 118 of transport mechanism 46.

In this position, transport mechanism 46 conveys bottle 48 into moisture analyzer 20' toward housing 42 (FIG. 8) and into proximity of heater 54 (FIG. 1). When lid 114 abuts cover portion 108 (FIG. 8) of sleeve 42, sleeve 42 retracts along tracks 44 causing coaxial needle 34 (FIG. 8) to penetrate septum 52 (FIG. 8) and enter bottle 48. Once coaxial needle 34 enters bottle 48 carrier gas 24 continuously flowing from output orifice 60 (FIG. 8) begins absorbing moisture evaporating from sample material 50 (FIG. 8) in bottle 48.

Carrier gas 24 carrying moisture from sample material 50 is received at input orifices 62 and transported via second channel 64 (FIG. 3) of coaxial needle 34 (FIG. 3) to relative humidity sensor 70 (FIG. 1) where the moisture in carrier gas 24 is detected. Carrier gas 24 carrying moisture from sample material 50 is subsequently exhausted from analyzer 20. As discussed previously, mass flow signal 30 (FIG. 1) and percent relative humidity signal 72 (FIG. 1) are used by processor 32 (FIG. 1) to obtain a moisture figure related to the amount of volatile liquid, or moisture, in sample material 50.

In summary, the present invention teaches of a continuous flow moisture analyzer that utilizes a carrier gas such as nitrogen or dry oxygen in a sealed gas flow system. The sealed gas flow system is accomplished through a sleeve for enclosing a coaxial needle during a standby mode so that baseline moisture content readings may be obtained The sleeve is retractable, in an active mode, through the contact of a sealed bottle against the sleeve. As the sleeve retracts, the coaxial needle penetrates the septum of a bottle. The coaxial needle located in the bottle then employs the carrier gas to absorb evaporated volatile liquid, which is subsequently detected by a moisture sensor. This results in an analyzer that efficiently and accurately determines the moisture content in a sample of test material. In addition, the moisture analyzer accurately determines the moisture content in the sample material by substantially preventing the introduction of uncontrolled moisture in the gas flow system of the moisture analyzer.

Although the preferred embodiments of the invention have been illustrated and described in detail, it will be readily apparent to those skilled in the art that various modifications may be made therein without departing from the spirit of the invention or from the scope of the appended claims.

What is claimed is:

1. A continuous flow moisture analyzer comprising:
    a first needle portion having a first channel for receiving a carrier gas and having an output orifice from the first channel for expelling the carrier gas;
    a second needle portion having an input orifice for receiving the carrier gas expelled from the output orifice and having a second channel in communication with the input orifice for transporting the carrier gas;
    a housing for enclosing the output orifice and the input orifice when the moisture analyzer is in a standby mode so that the carrier gas can flow through the first channel and the second channel in the standby mode;
    a bottle for retaining a sample material when the moisture analyzer is in an active mode, the bottle having a septum configured to face the housing, the first and second needle portions penetrating the septum to position the output and input orifices in the bottle, the carrier gas expelled from the output orifice absorbing moisture from the sample material; and
    a moisture sensor in fluid communication with the second channel for detecting the moisture in the carrier gas.

2. A continuous flow moisture analyzer as claimed in claim 1 further comprising a pressure regulator in fluid communication with the first needle portion for providing the carrier gas to the first channel at a predetermined pressure.

3. A continuous flow moisture analyzer as claimed in claim 1 further comprising a valve in fluid communication with the first needle portion for providing the carrier gas to the first channel at a predetermined flow rate.

4. A continuous flow moisture analyzer as claimed in claim 1 further comprising a mass flow sensor in fluid communication with the first needle portion for measuring a flow rate of the carrier gas entering the first channel.

5. A continuous flow moisture analyzer as claimed in claim 4 wherein:
    the moisture sensor is a relative humidity sensor; and
    the analyzer further comprises a processor in communication with each of the relative humidity sensor and the mass flow sensor for computing a moisture content of the carrier gas with respect to a unit of time.

6. A continuous flow moisture analyzer as claimed in claim 1 further comprising a processor in communication with the moisture sensor, the processor computing a baseline moisture content of the carrier gas in the standby mode, the processor further computing a moisture content of the carrier gas in the active mode, and the processor determining a difference between the moisture content and the baseline moisture content to obtain a moisture figure of the sample material.

7. A continuous flow moisture analyzer as claimed in claim 1 wherein the first and second needle portions have a common longitudinal axis.

8. A continuous flow moisture analyzer as claimed in claim 1 wherein:
    the first needle portion exhibits an outer diameter; and
    the second channel of the second needle portion exhibits an inner diameter, the inner diameter being greater than the outer diameter, and the first needle portion being positioned within the second channel.

9. A continuous flow moisture analyzer as claimed in claim 8 wherein the first and second needle portions form a coaxial needle having an end configured to penetrate the septum of the bottle, the output orifice is proximate the end, and the input orifice is longitudinally offset along a longitudinal axis of the coaxial needle relative to the output orifice such that the input orifice is a greater distance from the end than the output orifice.

10. A continuous flow moisture analyzer as claimed in claim 8 wherein the first and second needle portions form a coaxial needle having a circumference, and the input orifice is circumferentially offset about the circumference relative to the output orifice such that the input orifice is out of alignment with the output orifice.

11. A continuous flow moisture analyzer as claimed in claim 1 wherein:
    the first channel exhibits a first cross-sectional gas flow area; and
    the second channel exhibits a second cross-sectional gas flow area, the second cross-sectional gas flow area being substantially equivalent to the first cross-sectional gas flow area.

12. A continuous flow moisture analyzer as claimed in claim 1 wherein:
    the bottle is configured to abut the housing; and
    the housing comprises:
        a track in non-moving relation with the first and second needle portions; and
        a sleeve slidably coupled to the track such that the sleeve retracts when the bottle abuts the sleeve to allow the first and second needle portions to penetrate the septum.

13. A continuous flow moisture analyzer as claimed in claim 1 wherein:.
    the first and second needle portions form a coaxial needle having a first end and a second end, the output orifice and the input orifice being located proximate the second end; and the housing comprises a sleeve having a first side and a second side, the coaxial needle extending through a first opening in the first side, and the second end of the coaxial needle blocking a second opening in the second side of the sleeve to form a sealed chamber within the sleeve in which the output orifice and the input orifice reside in the standby mode.

14. A continuous flow moisture analyzer as claimed in claim 13 wherein the housing further comprises:
   a first O-ring located in the first opening and surrounding the first end of the coaxial needle; and
   a second O-ring located in the second opening and surrounding the second end of the coaxial needle.

15. A continuous flow moisture analyzer as claimed in claim 13 wherein the second end of the coaxial needle protrudes through the second opening into the bottle in the active mode.

16. A continuous flow moisture analyzer as claimed in claim 1 further comprising a transport mechanism for conveying the bottle toward the housing so that the first and second needle portions penetrate a center portion of the septum.

17. A continuous flow moisture analyzer as claimed in claim 16 wherein the transport mechanism is adjustable for conveying the bottle having a first diameter and for conveying a second bottle having a second diameter, the second diameter differing from the first diameter.

18. A continuous flow moisture analyzer as claimed in claim 16 wherein the transport mechanism comprises:
   a base including an adjustment element;
   a top configured to face the housing; and
   retaining rods for holding the bottle, the retaining rods being movably coupled to the adjustment element of the base and movably coupled to the top, the retaining rods having an elbow at each of a first end and a second end, wherein when the adjustment element is actuated, the retaining rods concurrently pivot relative to the base and the top to bring the elbows near a center axis of the transport mechanism, and when the adjustment element is further actuated, the retaining rods concurrently pivot relative to the base and the top to bring the elbows away from a center axis of the transport mechanism.

19. A continuous flow moisture analyzer as claimed in claim 1 further comprising a heater surrounding the bottle for heating the sample material when the moisture analyzer is in the active mode.

20. A continuous flow moisture analyzer as claimed in claim 1 further comprising a filter interposed between the second channel of the second needle portion and the moisture sensor.

21. A continuous flow moisture analyzer comprising:
   a coaxial needle having a first end and a second end, the coaxial needle including:
      a first needle portion having a first channel for receiving a carrier gas and having an output orifice from the first channel for expelling the carrier gas; and
      a second needle portion having an input orifice for receiving the carrier gas expelled from the output orifice and having a second channel in communication with the input orifice for transporting the carrier gas, the output orifice and the input orifice being located proximate the second end;
   a housing for enclosing the output orifice and the input orifice when the moisture analyzer is in a standby mode, the housing including:
      a track in non-moving relation with the coaxial needle; and
      a sleeve slidably coupled to the track;
   a bottle for retaining a sample material and configured to abut the sleeve when the moisture analyzer is in an active mode, the bottle having a septum facing the sleeve, and when the bottle abuts the sleeve, the sleeve retracts along the track to allow the coaxial needle to penetrate the septum to position the output and input orifices in the bottle, the carrier gas expelled from the output orifice absorbing moisture from the sample material; and
   a moisture sensor in fluid communication with the second channel for detecting the moisture in the carrier gas.

22. A continuous flow moisture analyzer as claimed in claim 21 wherein:
   the first needle portion exhibits an outer diameter; and
   the second channel of the second needle portion exhibits an inner diameter, the inner diameter being greater than the outer diameter, and the first needle portion being positioned within the second channel.

23. A continuous flow moisture analyzer as claimed in claim 21 wherein:
   the first channel exhibits a first cross-sectional gas flow area; and
   the second channel exhibits a second cross-sectional gas flow area, the second cross-sectional gas flow area being substantially equivalent to the first gas. flow cross-sectional area.

24. A continuous flow moisture analyzer as claimed in claim 21 wherein:
   the sleeve includes a first side and a second side, the coaxial needle extending through a first opening in the first side, and the second end of the coaxial needle blocking a second opening in the second side of the sleeve to form a sealed chamber within the sleeve in which the output orifice and the input orifice reside in the standby mode.

25. A continuous flow moisture analyzer as claimed in claim 24 wherein the housing further comprises:
   a first O-ring located in the first opening and surrounding the first end of the coaxial needle; and
   a second O-ring located in the second opening and surrounding the second end of the coaxial needle.

26. A continuous flow moisture analyzer as claimed in claim 24 wherein the second end of the coaxial needle protrudes through the second opening into the bottle in the active mode.

27. A continuous flow moisture analyzer as claimed in claim 24 further comprising a transport mechanism for conveying the bottle toward the housing so that the first and second needle portions penetrate a center portion of the septum.

28. A continuous flow moisture analyzer comprising:
   a first needle portion having a first channel for receiving a carrier gas and having an output orifice from the first channel for expelling the carrier gas;
   a second needle portion having an input orifice for receiving the carrier gas expelled from the output orifice and having a second channel in communication with the input orifice for transporting the carrier gas;
   a housing for enclosing the output orifice and the input orifice when the moisture analyzer is in a standby mode, the housing including:

a track in non-moving relation with the first and second needle portions; and a sleeve slidably coupled to the track;

a bottle for retaining a sample material when the moisture analyzer is in an active mode, the bottle having a septum configured to face the housing;

a transport mechanism for conveying the bottle toward the housing so that the first and second needle portions penetrate a center portion of the septum to position the output and input orifices in the bottle, the carrier gas expelled from the output orifice absorbing moisture from the sample material; and a moisture sensor in fluid communication with the second channel for detecting the moisture in the carrier gas.

29. A continuous flow moisture analyzer as claimed in claim 28 wherein the transport mechanism is adjustable for conveying the bottle having a first diameter and for conveying a second bottle having a second diameter, the second diameter differing from the first diameter.

30. A continuous flow moisture analyzer as claimed in claim 28 wherein the transport mechanism comprises:

a base including an adjustment element;

a top configured to face the housing; and retaining rods for holding the bottle, the retaining rods being movably coupled to the adjustment element of the base and movably coupled to the top, the retaining rods having an elbow at each of a first end and a second end, wherein when the adjustment element is actuated, the retaining rods concurrently pivot relative to the base and the top to bring the elbows near a center axis of the transport mechanism, and when the adjustment element is further actuated, the retaining rods concurrently pivot relative to the base and the top to bring the elbows away from a center axis of the transport mechanism.

* * * * *